United States Patent [19]

Horton

[11] 4,410,342
[45] Oct. 18, 1983

[54] METHOD AND APPARATUS FOR SEPARATING A LIQUID PRODUCT FROM A HYDROCARBON-CONTAINING GAS

[75] Inventor: John L. Horton, Shreveport, La.

[73] Assignee: United States Riley Corporation, Shreveport, La.

[21] Appl. No.: 381,215

[22] Filed: May 24, 1982

[51] Int. Cl.³ .............................................. F25J 3/02
[52] U.S. Cl. ............................................. 62/23; 62/39
[58] Field of Search ...................... 62/9, 11, 23, 38, 39

[56] References Cited

U.S. PATENT DOCUMENTS 3,373,574  3/1968  Fisher ...................................... 62/23
3,675,435  7/1972  Jackson et al. .......................... 62/28

Primary Examiner—Frank Sever
Attorney, Agent, or Firm—Mason, Kolehmainen, Rathburn & Wyss

[57] ABSTRACT

A method and apparatus is disclosed for separating a liquid product from a hydrocarbon-containing feed gas, such as natural gas, including introducing the feed gas to a heat exchanger; cooling the feed gas in the heat exchanger to condense a portion of the feed gas to form a first vapor fraction and a rich liquid fraction; flowing the first vapor fraction at a predetermined inlet pressure through an expansion valve to reduce the pressure of the first vapor fraction to a pressure at or below ⅓ of the expansion valve inlet pressure; flowing the rich liquid fraction through a second expansion valve to reduce the pressure of the rich liquid fraction to a pressure at or below ⅓ of the second expansion valve inlet pressure; introducing the cooled first vapor fraction and the cooled rich liquid fraction into the heat exchanger for indirect heat-exchange with the feed gas to cool the feed gas; removing the rich gas from the heat exchanger; condensing a portion of the rich gas to form a liquid product and a rich vapor fraction; and adding the rich vapor fraction to the feed gas and recycling the rich vapor fraction, in admixture with the feed gas, to the heat exchanger.

15 Claims, 2 Drawing Figures

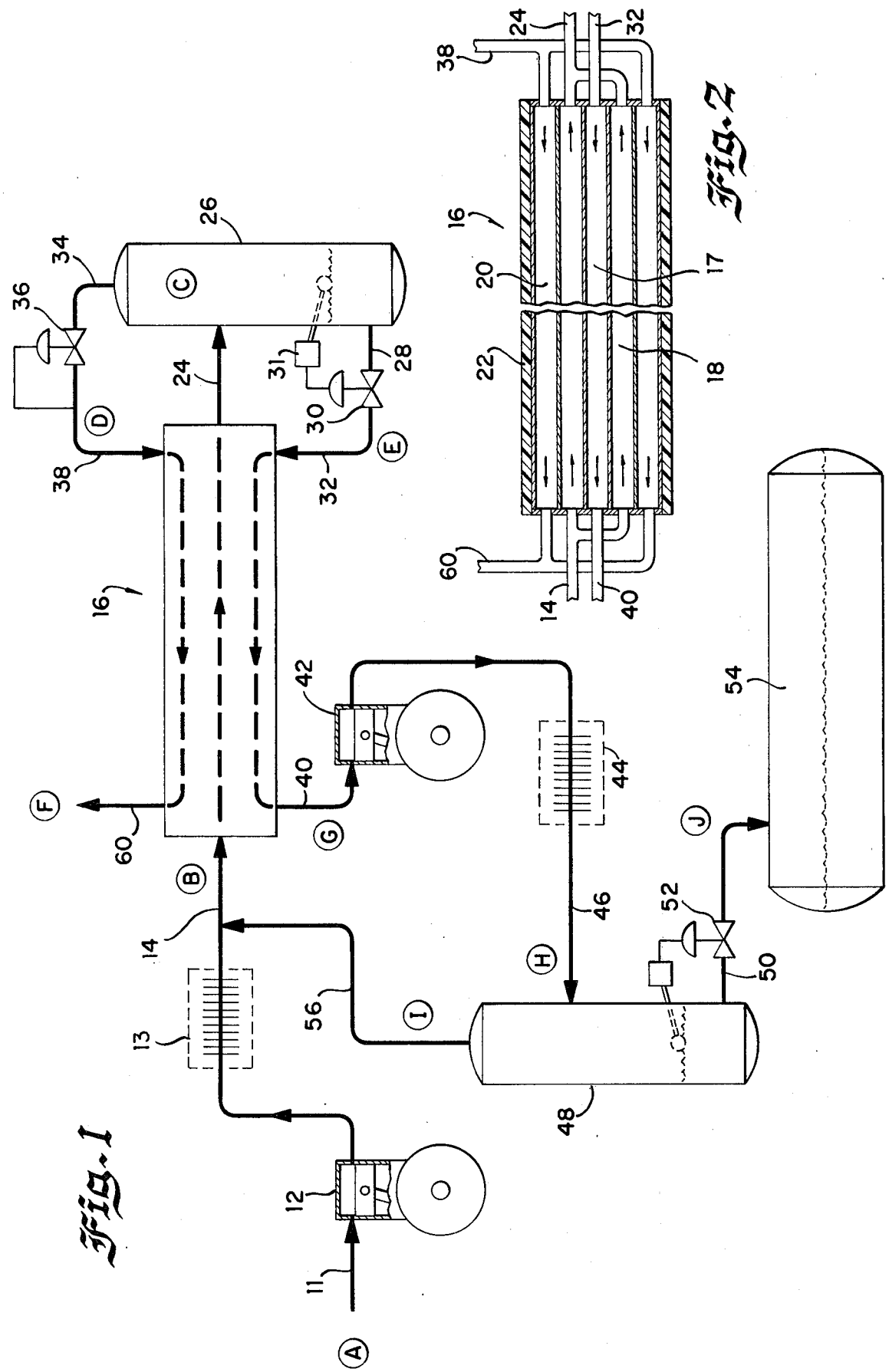

4,410,342

METHOD AND APPARATUS FOR SEPARATING A LIQUID PRODUCT FROM A HYDROCARBON-CONTAINING GAS

FIELD OF THE INVENTION

The present invention relates to a method and apparatus for separating a fraction, in liquid form, from a hydrocarbon gas stream and, more particularly, relates to a method and apparatus for separating a natural gas stream into a fuel gas product having a heating value generally in the range of 950–1050 BTU and a liquid product stream obtained by compressing and cooling a rich gas stream to a predetermined temperature and pressure to form a mixture of vapor and liquid, collecting the liquid as product, and recycling the vapor through the process by adding the recycled vapor to the incoming natural gas.

BACKGROUND OF THE INVENTION AND PRIOR ART

My prior U.S. Pat. No. 3,398,543 describes a method and apparatus for separating various components from natural gas, in vapor form, by regenerative cooling thereof under substantially constant enthalpy conditions. In accordance with my prior patent, a rich gas stream is collected as product generally corresponding in composition to stream G set forth in the Table of the instant application.

SUMMARY OF THE INVENTION

In accordance with my prior U.S. Pat. No. 3,398,543, a rich gas stream is obtained as a gaseous product by cooling a feed gas in an intermediate passage of a concentric three passage heat exchanger to condense a portion of the hydrocarbons from the feed gas thereby converting the feed gas into a vapor fraction and a liquid fraction. The vapor fraction is educted through an expansion valve and the liquid fraction, together with a small amount of vapor, is educted through another expansion valve and the expanded, cooled fractions are passed countercurrently to the feed gas through the other two passages of the concentric three passage heat exchanger thereby cooling and partially condensing the incoming feed gas and vaporizing the liquid fraction to form a vaporized, rich gas product. In accordance with the present invention, it has been found that a leaner product can be obtained by compressing and cooling the rich gas stream out of the three passage heat exchanger to a predetermined temperature and pressure to obtain a vapor fraction and a predetermined liquid product and recycling the vapor fraction with the raw inlet gas through the three passage heat exchanger.

Accordingly, an object of the present invention is to provide a new and efficient method and apparatus for separating a hydrocarbon fraction, in liquid form, from a hydrocarbon-containing gas.

Another object of the present invention is to provide a new and improved method and apparatus for separating a liquid hydrocarbon fraction product from a hydrocarbon-containing feed gas by cooling the gas to condense a portion of the gas, thereby forming a first liquid fraction and a first vapor fraction, separating the first liquid fraction from the first vapor fraction, vaporizing the first liquid fraction to form a second vapor fraction, condensing a portion of the second vapor fraction to form the liquid hydrocarbon fraction product and a third vapor fraction, and recycling the third vapor fraction with the feed gas.

Another object of the present invention is to provide a new and improved method and apparatus for separating a predetermined fraction from a raw inlet gas by cooling the raw inlet gas by indirect heat-exchange contact with an expanded, cooled first vapor fraction of the raw inlet gas and a cooled first liquid fraction of the raw inlet gas. In this manner, the raw inlet gas is substantially cooled to condense a portion of the gas thereby forming the first vapor fraction and first liquid fraction for expansion and regenerative cooling of the raw inlet gas and heat-exchange vaporization of the first liquid fraction. The vaporized first liquid fraction is then compressed and cooled to a predetermined temperature and pressure to condense a liquid product, and an uncondensed portion of the liquid fraction is recycled with the raw inlet gas for heat-transfer with the first liquid fraction and first vapor fraction.

These and other objects and advantages will become apparent from the following detailed description of the invention described with reference to the drawing, wherein:

BRIEF DESCRIPTION OF THE DRAWING

FIG. 1 is a schematic flow diagram of the method and apparatus of the present invention.

FIG. 2 is a cross sectional view of the three passage heat exchanger of FIG. 1.

DETAILED DESCRIPTION OF A SPECIFIC EMBODIMENT

Referring now to the drawing, a raw inlet gas, such as natural gas, is introduced through conduit 11, compressed to a pressure of 230 psig in compressor 12, and cooled to a temperature of 120° F. in cooler 13. The pressurized, cooled gas proceeds through conduit 14 into a concentric three passage heat exchanger, generally designated by reference numeral 16. In the drawing, points A through J are identified and correspond to data points A through J in the following Table where the stream at each point is identified in terms of temperature, pressure, vapor or liquid, flow rate and composition. The heat exchanger 16, includes a central annular passage 17; an intermediate annular passage 18 and an outer annular passage 20. An external layer of heat insulating material 22 preferably is applied to an outer periphery of the heat exchanger 16. The raw inlet gas is conveyed through the intermediate passage 18 of the heat exchanger 16 where the raw gas is in indirect, heat-exchange contact with the central heat exchange passage 17 and the outer heat exchange passage 20. Freezing can be avoided, as disclosed in my prior U.S. Pat. No. 3,398,543, by adding an antifreeze, such as methanol, to the raw inlet gas before the gas enters the heat exchanger 16.

The raw inlet gas is substantially cooled in the intermediate heat exchange passage 18 to about −20° F. where the inlet gas is partially condensed as a result of regenerative cooling from heat exchanger passages 17 and 20. The raw inlet gas leaves the heat exchanger 16 as a mixture of vapor and liquid through conduit 24 and the vapor and liquid mixture is collected in a cold separator vessel 26. The heavier components of the inlet gas stream are collected in cold separator 26 as a liquid fraction and the lighter components of the inlet gas are collected in the cold separator 26 as a vapor fraction.

The liquid fraction collected at the bottom of the cold separator 26 leaves the separator 26 via conduit 28 through expansion valve 30 and conduit 32 into the central heat exchange passage 17 in countercurrent flow to the inlet gas stream through intermediate heat exchanger passage 18 to achieve regenerative cooling and partial condensation of the raw inlet gas.

Expansion valve 30 operates automatically by float control 31 once a liquid level is established in the cold separator 26. However, to establish the cooling required to condense a major portion of the raw inlet gas in start-up, for the purpose of obtaining a liquid level in separator 26, the expansion valve 30 can be opened manually so that initially a combination of vapor and liquid is educted through expansion valve 30. Once a liquid level is established in separator 26 and equilibrium is obtained in the heat exchanger 16, the expansion valve 30 operates automatically, educting only liquid.

The pressure in conduit 28 is substantially (at least three times) greater than the pressure in conduit 32 so that the liquid from the cold separator 26 is substantially expanded and cooled due to the Joule-Thomson effect and, because of this expansion, a portion of the liquid from the cold separator 26 is vaporized at the outlet of the expansion valve 30 so that a mixture of vapor and liquid at relatively low temperature, i.e. $-69°$ F., enters the central heat exchanger passage 17 for regenerative heat exchange with the incoming raw gas. Similarly, the vapor fraction from the cold separator 26 exits the cold separator 26 via conduit 34 and passes through expansion valve 36 where the light vapors from the cold separator 26 are expanded and thereby cooled, i.e. $-38°$ F., by the Joule-Thomson effect as the light vapors proceed from conduit 34 through the expansion valve 36 into conduit 38 maintained at a pressure substantially below (at least three times lower than) the pressure in conduit 34.

To achieve the full advantage of the present invention, the pressure on the inlet side of the expansion valves 30 and 36 should be at least three times, and preferably at least five times the pressure on the outlet side of the expansion valves. This substantial change in pressure permits the expanded liquid and gas streams to cool sufficiently to achieve a desirable liquid fraction in cold separator 26 for recycle in accordance with the principles of the present invention.

The cooled ($-38°$ F.), light vapors in conduit 38 are directed into the outer passage 20 of the heat exchanger 16 for heat exchanger with the countercurrently flowing inlet gas in intermediate heat exchange passage 18. The separately expanded and cooled vapor and liquid fractions from cold separator 26, flowing countercurrently to the incoming raw gas, are superheated by heat exchange with the incoming raw gas. The liquid fraction from cold separator 26 is superheated within central heat exchange passage 17 and exits the heat exchanger 14 through conduit 40 as a rich gas. The rich gas in conduit 40 is compressed to a predetermined pressure in compressor 42 and cooled to a predetermined temperature in cooler 44, generally to achieve the same temperature and pressure as the inlet gas entering the heat exchanger 16, to condense a heavier portion of the rich gas stream, to obtain a rich liquid product and a lighter or second vapor portion of the rich gas stream for recycling to the heat exchanger 16. The rich vapor and rich liquid from cooler 44 is conveyed through conduit 46 to a product separator vessel 48 and the rich liquid portion is withdrawn from the product separator 48 through conduit 50, and flow control valve 52 for storage in a product storage vessel 54.

In accordance with an important feature of the present invention, the vapor from product separator 48 is conveyed through a recycle conduit 56 and joins the inlet feed gas in conduit 14 so that both the inlet feed gas and the recycled rich gas from the product separator are conveyed into the intermediate passage 18 of the heat exchanger 16. In accordance with my prior U.S. Pat. No. 3,398,543, the product stream was obtained as a gas out of the heat exchanger 16. In accordance with an important feature of the present invention, the rich gas in conduit 40 is compressed and cooled to cause condensation of a portion of the rich gas to form a rich liquid product, and the vapor portion of the condensed and cooled rich gas is recycled back to the heat exchanger 16 together with the raw inlet gas.

The recycling of the rich vapor portion from product separator 48 changes the equilibrium of the raw inlet gas within the heat exchanger 16 by recycling a lighter portion of the rich gas from the heat exchanger 16 to obtain a higher concentration of butane—heptane in the liquid product. Further, recycling of the vapor portion of the rich gas from the product separator 48 into the heat exchanger 16 enables better separation of the methane from the rich gas so that the methane forms a higher concentration of the fuel gas leaving the outer passage 20 of the heat exchanger 16 through conduit 60. Further, by virtue of the recycling of the vapor from product separator 48, nitrogen and carbon dioxide are virtually eliminated from the liquid product, while providing a gaseous product or fuel gas having a heating value in the desirable range of 950–1050 BTU.

As shown in the following table indicating temperature, pressure, vapor or liquid or mixture, and composition of the material at various points along the apparatus of the present invention, it is seen by comparing the composition at point G—the rich gas exiting the heat exchanger 16—to point J—the liquid product obtained in accordance with the present invention—the concentration of butane—pentane is substantially increased and the concentration of ethane substantially decreased in accordance with the partial condensation and rich vapor recycling of the present invention.

TABLE

| Stream | A | B | C | D | E | F | G | H | I | J |
|---|---|---|---|---|---|---|---|---|---|---|
| Pressure (psig) | 50 | 230 | 230 | 68 | 18 | 68 | 18 | 230 | 230 | 230 |
| Temperature (°F.) | 120° | 120° | $-20°$ | $-38°$ | $-69°$ | 103° | 112° | 120° | 120° | 120° |
| Vapor or Liquid | V | V | V & L | V | V & L | V | V | V & L | V | L |
| Mcfd | 964 | 1064 | 1064 | 848 | 215 | 848 | 215 | 215 | 100 | 115 |
| Mole Fract. | | | | | | | | | | |
| $N_2$ | .0294 | .0271 | .0271 | .0336 | .0027 | .0336 | .0027 | .0027 | .0032 | — |
| $CO_2$ | .0024 | .0023 | .0023 | .0023 | .0024 | .0023 | .0024 | .0024 | .0020 | .0003 |
| $C_1$ | .6770 | .6325 | .6325 | .7667 | .1272 | .7667 | .1272 | .1272 | .1988 | .0173 |

TABLE-continued

| Stream | A | B | C | D | E | F | G | H | I | J |
|---|---|---|---|---|---|---|---|---|---|---|
| C$_2$ | .1280 | .1432 | .1432 | .1360 | .1707 | .1360 | .1707 | .1707 | .2925 | .0886 |
| C$_3$ | .0853 | .1090 | .1090 | .0509 | .3264 | .0509 | .3264 | .3264 | .3396 | .3234 |
| iC$_4$ | .0140 | .0171 | .0171 | .0036 | .0680 | .0036 | .0680 | .0680 | .0456 | .0912 |
| nC$_4$ | .0340 | .0389 | .0389 | .0058 | .1635 | .0058 | .1635 | .1635 | .0882 | .2384 |
| iC$_5$ | .0104 | .0106 | .0106 | .0006 | .0482 | .0006 | .0482 | .0482 | .0137 | .0808 |
| nC$_5$ | .0117 | .0119 | .0119 | .0005 | .0559 | .0005 | .0559 | .0559 | .0133 | .0949 |
| C$_6$ | .0057 | .0056 | .0056 | — | .0264 | — | .0264 | .0264 | .0027 | .0487 |
| C$_{7+}$ | .0021 | .0018 | .0018 | — | .0086 | — | .0086 | .0086 | .0004 | .0164 |

Comparison of the composition of the gas stream out of the heat exchanger at G (Table) to the composition of the liquid product of the present invention at J shows that recycling the rich gas from the product separater 48 to the intermediate passage 18 of the heat exchanger 16, substantially decreases the whole percentage of ethane in the product by about 50%, increases the mole percentage of isobutane from 6.8% to 9.12%, and that of normal butane from 16.35% to 23.84%; increases the mole percentage of isopentane from 4.82% to 8.08%, and that of normal pentane from 5.6% to 9.5%. In the specific embodiment shown, it has been found that the liquid product having an ethane mole percentage less than about 10%; propane mole percentage of at least 30%; butane (iso and normal) mole percentage of at least 30%; and pentane (iso and normal) mole percentage of at least 15% is very desirable for good anti-knock ratings in gasoline for Otto cycle engines when the liquid product is further processed into gasoline. Further, the liquid product is valuable for butane and pentane separation. To achieve the full advantage of the present invention, however, the liquid product contains in mole percent, ethane: about 5%–10%; propane about 30%–35%; butane: about 30%–35%; and pentane: about 15%–20%.

While the above described invention has been described with respect to a specific embodiment, certain modifications would be obvious to those skilled in the art and are intended to be included within the scope hereof.

What is claimed as new and desired to be secured by Letters Patent of the United States is:

1. A method of separating a liquid product from a hydrocarbon-containing feed gas comprising
   introducing the feed gas to a heat exchanger;
   cooling said feed gas in said heat exchanger to condense a portion of said feed gas to form a first vapor fraction and a rich liquid fraction;
   flowing said first vapor fraction at a predetermined inlet pressure through an expansion valve to reduce the pressure of said first vapor fraction to a pressure at or below $\frac{1}{3}$ of the expansion valve inlet pressure, thereby substantially cooling said first vapor fraction;
   flowing said rich liquid fraction at a predetermined inlet pressure through a second expansion valve to reduce the pressure of said rich liquid fraction to a pressure at or below $\frac{1}{3}$ of the second expansion valve inlet pressure, thereby substantially cooling said rich liquid fraction;
   introducing said cooled first vapor fraction and said cooled rich liquid fraction into said heat exchanger for indirect heat-exchange with said feed gas to cool said feed gas, to heat said cooled first vapor fraction and to heat said rich liquid fraction to form a rich gas;
   removing said rich gas from said heat exchanger;
   condensing a portion of said rich gas to form a liquid product and a rich vapor fraction; and
   adding said rich vapor fraction to said feed gas and recycling said rich vapor fraction, in admixture with said feed gas, to said heat exchanger to decrease the concentration of the ligher hydrocarbons in the liquid product.

2. The method of claim 1 wherein said mixture of recycled rich gas and feed gas is introduced into said heat exchanger at a pressure of at least 100 psig, and wherein substantially only said rich gas is recycled.

3. The method of claim 2 wherein the pressure ratio across the expansion valves is at least 5:1.

4. The method of claim 1 wherein said feed gas comprises natural gas, and at least 90% of said liquid product comprises ethane to hexane molecules.

5. The method of claim 1 wherein ethane is present in the liquid product in an amount of 10 mole percent or less.

6. The method of claim 1 wherein butanes are present in the liquid product in an amount of at least 30 mole percent.

7. The method of claim 1 wherein pentanes are present in the liquid product in an amount of at least 15 mole percent.

8. The method of claim 1 wherein the mole percent of the liquid product comprises:
   C$_2$: 5–10%
   C$_3$: 30–35%
   C$_4$: 30–35%
   C$_5$: 15–20%
   C$_6$: 1–10%.

9. The method of claim 1 wherein said first vapor fraction and said first liquid fraction are separately expanded across different expansion valves having a pressure ratio across said valves of at least 3:1.

10. A method of separating a heavier fraction and a ligher fraction from a hydrocarbon-containing feed comprising:
    introducing the feed into an intermediate passage of a heat exchanger and cooling said feed from surrounding passages of said heat exchanger to partially condense said feed to form a first liquid fraction and a first vapor fraction;
    collecting said first liquid fraction and said first vapor fraction in a separator vessel;
    separately expanding said first vapor fraction and said first liquid fraction to cool said first vapor fraction and said first liquid fraction;
    introducing said cooled first vapor fraction and said cooled first liquid fraction into said surrounding passages of said heat exchanger to flow countercurrently to said feed to heat said first vapor fraction and said first liquid fraction, to vaporize at least a portion of said first liquid fraction and to cool said feed;

removing said heated first vapor fraction from said heat exchanger as a gaseous product;

removing said heated first liquid fraction from said heat exchanger and condensing at least a portion of said first liquid fraction vapors to form a liquid product fraction and a second vapor fraction and recirculating said second vapor fraction through said intermediate passage of said heat exchanger to decrease the concentration of the lighter hydrocarbons in the liquid product.

11. A method of separating a hydrocarbon feed into a liquid heavier fraction and a lighter vapor fraction comprising:

introducing the feed into an intermediate passage of a heat exchanger and cooling said feed from surrounding passages of said heat exchanger to partially condense said feed to form a first liquid fraction and a first vapor fraction;

cooling said first vapor fraction and said first liquid fraction;

introducing said cooled first vapor fraction and said cooled first liquid fraction into said surrounding passages of said heat exchanger to heat said first vapor fraction and said first liquid fraction, to vaporize at least a portion of said first liquid fraction and to cool said feed;

removing said heated first vapor fraction from said heat exchanger as said lighter vapor fraction;

removing said heated first liquid fraction from said heat exchanger and condensing at least a portion of said vapors from said first liquid fraction to form said heavier liquid fraction and a second vapor fraction and recirculating said second vapor fraction through said intermediate passage of said heat exchanger to increase the concentration of the lighter hydrocarbons in the lighter vapor fraction.

12. The method of claim 11 wherein said first vapor fraction and said first liquid fraction are separately expanded across different expansion valves having a pressure ratio across said valves of at least 3:1.

13. A method of separating a liquid and a vapor from a hydrocarbon-containing feed gas comprising introducing the feed gas to a heat exchanger;

cooling said feed gas in said heat exchanger to condense a portion of said feed gas to form a first vapor fraction and a rich liquid fraction;

cooling said first vapor fraction and said rich liquid fraction;

introducing said cooled first vapor fraction and said cooled rich liquid fraction into said heat exchanger for indirect heat-exchange with said feed gas to cool said feed gas, to heat said cooled first vapor fraction and to heat said rich liquid fraction to form a rich gas;

removing said rich gas from said heat exchanger;

removing said first vapor fraction from said heat exchanger;

condensing a portion of said rich gas to form a liquid fraction and a rich vapor fraction; and adding said rich vapor fraction to said feed gas and recycling said rich vapor fraction, in admixture with said feed gas, to said heat exchanger to increase the concentration of light vapors in the first vapor fraction removed from the heat exchanger.

14. The method of claim 13 wherein recycling of the rich vapor fraction increases the concentration of $C_1$ to $C_3$ hydrocarbons in the first vapor fraction removed from the heat exchanger.

15. Apparatus comprising elements sized and arranged for separating a liquid product from a hydrocarbon-containing feed gas, including a heat exchanger having an inner passage, an intermediate passage and an outer passage;

means for introducing the feed gas into the intermediate passage of said heat exchanger for cooling said feed gas from said inner and outer heat exchanger passages to partially condense said feed gas within said heat exchanger, and to form a first vapor fraction and a rich liquid fraction;

means for separating said first vapor fraction and said rich liquid fraction;

a first expansion valve means for expanding and thereby cooling said first vapor fraction to form an expanded first vapor fraction;

a second expansion valve means for expanding and thereby cooling said rich liquid fraction to form an expanded rich liquid fraction;

means for counterflowing, with respect to said feed gas, said expanded first vapor fraction and said expanded rich liquid fraction, one through said inner passage of said heat exchanger and the other through the outer passage of said heat exchanger to cool said feed gas, to heat said expanded first vapor fraction, and to heat said expanded rich liquid fraction to form a rich gas;

means for removing said rich gas from said heat exchanger;

means for condensing a portion of said rich gas to form a liquid product and a rich vapor fraction; and means for recycling substantially only said rich vapor fraction back to said intermediate passage of said heat exchanger to decrease the concentration of the lighter hydrocarbons in the liquid product.

* * * * *